United States Patent
Haroutunian

(10) Patent No.: US 12,283,419 B2
(45) Date of Patent: Apr. 22, 2025

(54) SOLENOID DEVICE FOR CREATING AND DETECTING COMPLEX ELECTROMAGNETIC FIELDS

(71) Applicant: Gagik Greg Haroutunian, Beverly Hills, CA (US)

(72) Inventor: Gagik Greg Haroutunian, Beverly Hills, CA (US)

(*) Notice: Subject to any disclaimer, the term of this patent is extended or adjusted under 35 U.S.C. 154(b) by 231 days.

(21) Appl. No.: 17/737,993

(22) Filed: May 5, 2022

(65) Prior Publication Data

US 2022/0406507 A1 Dec. 22, 2022

Related U.S. Application Data

(60) Provisional application No. 63/184,758, filed on May 5, 2021.

(51) Int. Cl.
*H01F 7/16* (2006.01)
*A61N 2/02* (2006.01)

(52) U.S. Cl.
CPC .............. *H01F 7/1607* (2013.01); *A61N 2/02* (2013.01)

(58) Field of Classification Search
CPC ............ H01F 7/1607; H01F 2005/025; H01F 2005/006; H01F 6/06; H01F 2027/2833; H01F 27/2823; H01F 41/06; A61N 2/02
See application file for complete search history.

(56) References Cited

U.S. PATENT DOCUMENTS

| | | | | |
|---|---|---|---|---|
| 5,187,859 | A * | 2/1993 | Heim | H01F 41/048 29/605 |
| 6,239,760 | B1 * | 5/2001 | Van Voorhies | H01Q 11/08 343/866 |
| 6,552,530 | B1 * | 4/2003 | Vaiser | H01Q 7/00 324/226 |
| 2016/0300652 | A1 * | 10/2016 | Daibo | H01F 5/02 |
| 2018/0204671 | A1 * | 7/2018 | Arndt | H01F 6/06 |
| 2020/0365303 | A1 * | 11/2020 | Hamada | H01F 27/2823 |

* cited by examiner

*Primary Examiner* — Reinaldo Sanchez-Medina
(74) *Attorney, Agent, or Firm* — Robert R. Mallinckrodt

(57) ABSTRACT

A solenoid device for generating or detecting electrical or magnetic fields includes at least two solenoids combined into a solenoid structure. A two level solenoid structure is formed by helically wrapping a long and bendable primary solenoid around a secondary core to create a secondary solenoid which includes the primary solenoid as a part. If the secondary solenoid is bendable and long enough, it can be helically wrapped around a tertiary core to form a tertiary solenoid which contains the primary solenoid and the secondary solenoid as parts. The upper level solenoid will generally contain a hollow core into which items or bodies to be treated with electrical or magnetic fields can be inserted for treatment. Further, items having inherent magnetic or electrical fields or properties can be inserted into the hollow core so the inherent fields can be detected.

20 Claims, 8 Drawing Sheets

SOLENOID DEVICE FOR CREATING AND DETECTING COMPLEX ELECTROMAGNETIC FIELDS

BACKGROUND OF THE INVENTION

Field: The invention is in the field of applying electrical signals or electrical fields or magnetic signals or magnetic fields to various items or bodies and to detecting electrical or magnetic signals or fields generated by various items or bodies.

State of the Art: In many situations it is desirable to apply electrical signals or electrical fields or magnetic signals or magnetic fields having certain characteristics or parameters such as certain frequencies, pulse forms, intensities, directions, duty cycles, etc. to various items or bodies. One area of current interest is the application of electromagnetic fields and electrical signals to parts of the human body and to components of the human and other animal bodies. Numerous studies have demonstrated that application of electric currents (both AC and DC) may be a useful method of triggering desirable changes in living cells and tissues. Of special interest are effects of electricity and/or magnetism on tissue regeneration, stem cell differentiation, and on cancer cells. From accelerated wound healing, to altering/effecting cellular differentiation of different types of stem cells, to transforming non-stem cells into stem cells, from treating retinal eye disease (retinitis pigmentosa), to improved bone healing, to direct brain stimulation—the widest spectrum of therapeutic effects have been documented with the use of electricity (electromagnetic fields). Additionally, electricity may be used for physical separation of different molecules and cells from each other.

In particular, electricity and magnetism have been used to affect living organisms, tissues and cells for a long time. There are numerous instances in which they are used, in one form or another, to achieve some medical benefits. For example, rectangular AC electricity is being used for transcutaneous stimulation to achieve reduction of pain using a TENS (Transcutaneous Electro Neuro Stimulation) device. Electric signals are used for specific nerve stimulation, as well as for stimulation of the brain to achieve various desired effects. Electro-convulsive therapy is currently used for severe depression. A gentler electric stimulation of the brain is used for such conditions as Autism, ADHD, Developmental Delay, etc. Electric signals have been shown to help restore retinal cells in a condition known as Retinitis Pigmentosa. There are reports of electricity being effective in hair regrowth. Electric shock is used to restore the normal rhythm of the heart when it stops or when it becomes chaotic. Numerous studies have proven the ability of electric signals to have specific effects on different cells and tissues. For example, DC and certain kinds of AC electric signals were able to induce transformation of some stem cells into cells of different lineage, such as neurogenic, chondrogenic or osteogenic stem cells.

Magnetic fields are also known to induce changes that may be used to achieve medical benefits. For example, transcranial magnetic stimulation is an approved therapeutic modality. Magnetic fields are being effectively used for treating osteoporosis, a condition in which there is a reduction in bone density, and the magnetic fields are able to stimulate osteogenesis—an increase in bone tissue production.

There are numerous devices on the market that are designed to deliver the desired electric or magnetic signals to the cells, tissues and organs. The vast majority of electric devices are employing some variation of electrodes that come into direct contact with the tissues. The magnetic devices are also typically designed to have a magnetic surface that emits the magnetic field in the desired direction.

Because of the difficulties with bringing the electrodes to the cells on a microscopic scale, other techniques have been developed, such as salt water bridges, molecular scaffolds, and other means of directly connecting the cells with the electric device. There is also a box with electro-conductive walls that are in contact with a liquid inside the box that contains cells, the electric signals are brought to the walls and further conducted to these cells. There are a number of problems with current devices which have not been effectively overcome:

1. The direct contact of the cells/tissues with the electro-conductive material (usually metal) can cause tissue/cell damage due to electrolysis at the point of contact.
2. Certain areas of the tissues in the body are not readily available for reaching with electrodes, as they may be surrounded with high value cells and tissues that can be damaged when electrodes are passed through them. For example, it is hard or impossible to apply electrodes to certain parts of the brain because the electrodes would have to go through (and potentially cause damage to) many layers of the brain tissues, which can cause permanent impairment and loss of function to the patient.
3. When electrodes (typically two) are applied to an organ or tissue, the path of the flow of electric signals within that organ or tissue is limited to either a single line or to a limited area between the electrodes. Adding more electrodes, however technically challenging, may still not achieve a creation of a complex 3-dimensional electric (electro-magnetic) field within the desired area, and may not reach all of the cells in that area.
4. Using magnetic fields doesn't achieve the creation of electric fields with specific lines of force that are congruent with a tissue's own electric orientation, which can be 3-dimensionally complex.
5. Many cells, tissues and organs are electrically polarized, which means that regardless of their structural symmetries they may also have electrical and/or magnetic axes of symmetry. The importance of this fact is hard to underestimate. The practical importance of such great variability of symmetries is apparent when one attempts to use electricity for therapeutic purposes. The direction of flow of electricity and its predictability may be of significance in that case.

Similar to the devices for delivering electro-magnetic signals to the cells, there are also devices for registering and measuring electro-magnetic phenomena induced within or produced by cells, tissues or organs. The best known such devices are ECG (electro-cardio-graphy) and EEG (electro-encephalo-graphy) machines which are designed to register the electric signals coming from the heart or the brain to the surface of the skin, from where they are picked up by the electrodes of the registering device. Although usually multiple electrodes are used to register signals from different parts of the respective organ, the information obtained does not fully reflect the complex 3-dimensional nature of the electric/electro-magnetic fields within that organ. There are numerous other devices used, ranging from simple volt and ampere meters to devices for Nerve Conduction Studies, and others, none of which is designed to obtain a complex 3-dimensional representation of the EMF within the tissue in study.

There is a need for a device that can generate desired and controlled electromagnetic fields and current flow in items or bodies without contact with the item or body. Further, it would be desirable that such a device could provide controlled desired symmetries and variations to the forces applied. Also, there is a need for devices that can detect and characterize complex three dimensional electromagnetic fields and signals within items of interest.

SUMMARY OF THE INVENTION

According to the invention, a device to create desired electromagnetic fields and current flows within an item or body without contact with the item or body comprises a device having a multi level fractal geometry comprising a primary helical winding including a primary thread wrapped helically around a primary core and at least one additional helical winding made by winding the primary helical winding around an additional or secondary core. This forms a secondary helical winding which can be said to have three levels of organization: 1. the thread, 2. the primary helical winding, and 3. the secondary helical winding which creates the secondary core. This secondary core can include an open space which can serve as a receiving chamber to receive items or bodies to be treated. Alternately, if the secondary helical winding is flexible enough and has a length sufficiently longer than its diameter it can be helically wound around an additional or tertiary core to form a tertiary helical winding which includes both the primary helical winding and the secondary helical winding. This gives the tertiary winding four levels of organization. With the tertiary helical winding, the tertiary core can include an open space which can serve as a receiving chamber to receive the items or bodies to be treated. Additional similar helical windings can be formed to create devices of the invention having higher levels of organization, if desired. This iterative process of coiling of the existing helix into another helix can be continued as long as the structure remains flexible enough, and its length is sufficiently long to be coiled into loops.

To describe the process of creating such a coil let's take a very long wire, which should be sufficiently flexible, have a cylindrical shape with the same diameter at any cross-section, should be made of electro-conductive material (has significant electric conductivity, such as copper), and its length should be many times larger than its diameter (L>>>D). Now let's coil this Wire around a real or imaginary cylinder (for example, around another wire of arbitrary diameter) in such a manner that there are no spaces between the loops, to become a helix tightly wound around a cylinder. Let's call it a primary helix. If the cylinder inside it is not rigid, then it can be flexed to give it any desired shape. Provided that the length of the primary helix is far larger than its diameter, we can now coil the primary helix around another cylinder of arbitrary diameter so that the loops are tightly wound leaving no spaces between them. This will create yet another helical structure, the secondary helix, which has the primary helix as its component. This secondary helix has a long axis which coincides with that of the cylinder it is wound around, and can be a straight line, or, if flexible enough, may be given different shapes. The axis of the primary helix is no longer a straight line, but now has a helical structure. The secondary helix is a complex structure that contains all the others as its components. It can be said that it has 3 levels of organization: 1. the wire, 2. the primary helix, 3. the secondary helix.

If the secondary helix is flexible enough and has a length sufficiently longer than its diameter (L>>>D), then it can be further flexed into yet another helical structure which we'll call a tertiary helix, and which would have 4 levels of organization, and all of the previous levels of organization would be included in it as its components.

This iterative process of coiling of the existing helix into another helix can be continued as long as the structure remains flexible enough, and its length is sufficiently long to be coiled into loops. The final product will be a helical structure with multiple levels of organization, all of which are similar to each other. We can create an entire class of coils that have this kind of iterative structure, they can have different levels of organization, as well as different lengths and diameters at each level.

Although the single wire used to build the entire construct is made of the same material at every level of organization, the cylindrical core around which each helix is wound can be made of different materials with different physical properties, and can have different diameters and lengths. If the core of the primary helix is made of a material with a high magnetic permeability (such as iron wire), then the primary helix will function as a solenoid—when electricity is applied to the ends of the copper wire, there will appear a magnetic field in its iron core. And if the core of the secondary helix is made of electro-conductive material (copper), then the magnetic field within the iron core of the primary helix will induce an electric field within the core of the secondary helix.

If all cores of all helices are each made into a closed loop, and if they are made of material that alternatively either has high magnetic permeability (e.g. iron) or high electro-conductivity (e.g. copper), then applying alternating electricity to the ends of the main wire will sequentially induce magnetic and electric fields in the alternating cores. It should be noted that while the alternating cores of the magnetic material have been indicated as made into closed loops, it is not necessary to close the loops of the magnetic material since the magnetic fields can close themselves without being physically closed. It is necessary to actually physically close the loops of the electrically conductive material.

While some of the characteristics of these fields may be the same (frequency), the directions of each of the fields induced in each of the loops in each of the helices will vary greatly, creating a very complex EMF with components in many directions in the 3D space.

Alternatively, the cells and tissues placed within the coil's space may produce electro-magnetic fields as a result of their own biological, physiologic, or metabolic activities, which will then induce electro-magnetic fields within the coils of the device, and can be subsequently detected and measured, or otherwise registered. In that case the coils will serve as receiving antennas. If a cell or a tissue with its own EMF is placed within this device, the registration of electric or magnetic signals from its different loops will potentially provide information about particular spatial component of that cell's or tissue's EMF, creating an opportunity to obtain a 3D representation of that complex EMF.

The basic physical principle used in the device of the invention is the induction of an alternating magnetic field by moving electric charges (alternating electric current from an external source applied to the wire of the coil), which then induces alternating electric fields within the defined space in the coil. This provides electrical currents in the defined space and in the items in the defined space without physical contact with the item in the defined space. This delivery of electricity without a direct mechanical contact with the wire of the coil may be important for avoiding some of the well-known problems that emerge when contact electrodes are used, such as electrolysis and chemical reactions with the metallic electrode, mechanical tissue damage, poor contact with the cells, inability to bring the tip of the electrode to the desired point in space due to natural barriers, etc.

BRIEF DESCRIPTION OF THE DRAWINGS

Additional features and advantages of the invention will be apparent from the detailed description which follows, taken in conjunction with the accompanying drawings, which together illustrate, by way of example, features of the invention, and wherein.

DETAILED DESCRIPTION OF THE ILLUSTRATED EMBODIMENTS

Figure 1:
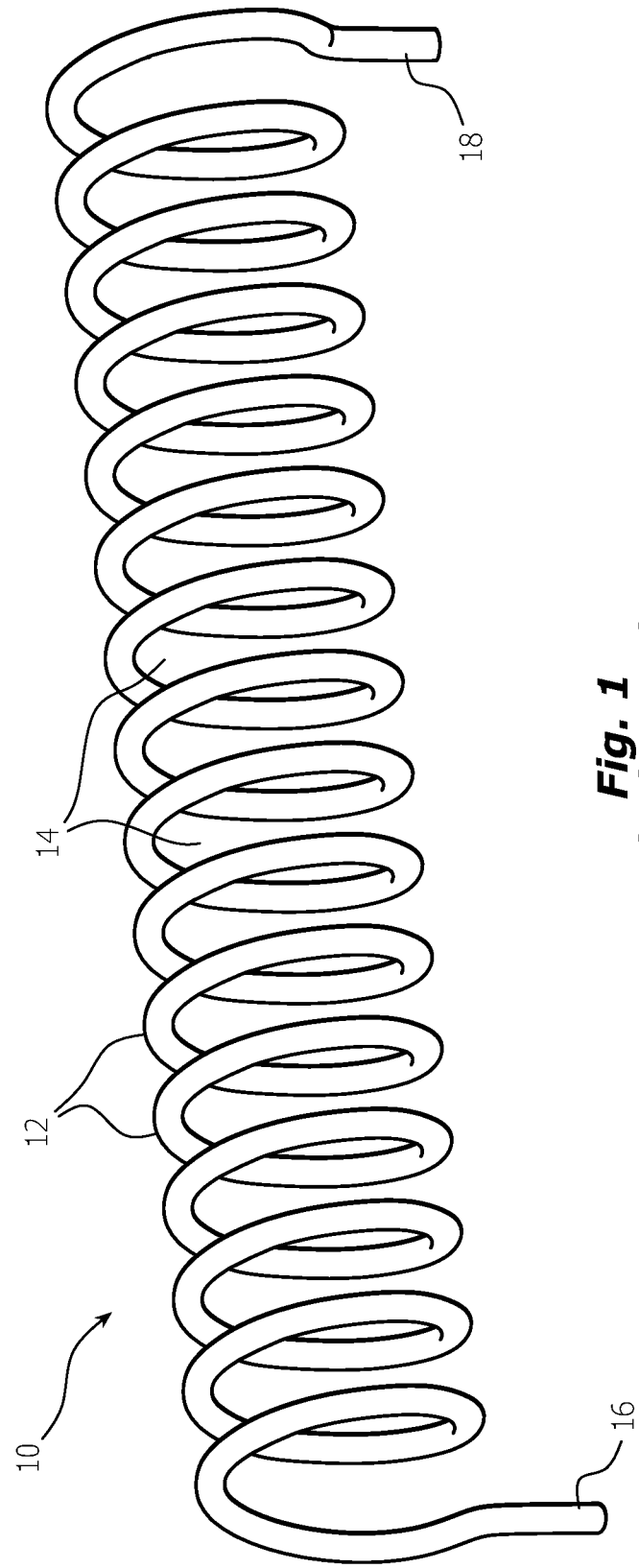
FIG. 1 shows a copper wire wound into a helical coil, also referred to as a solenoid. This represents a solenoid of the prior art.
Figure 2:
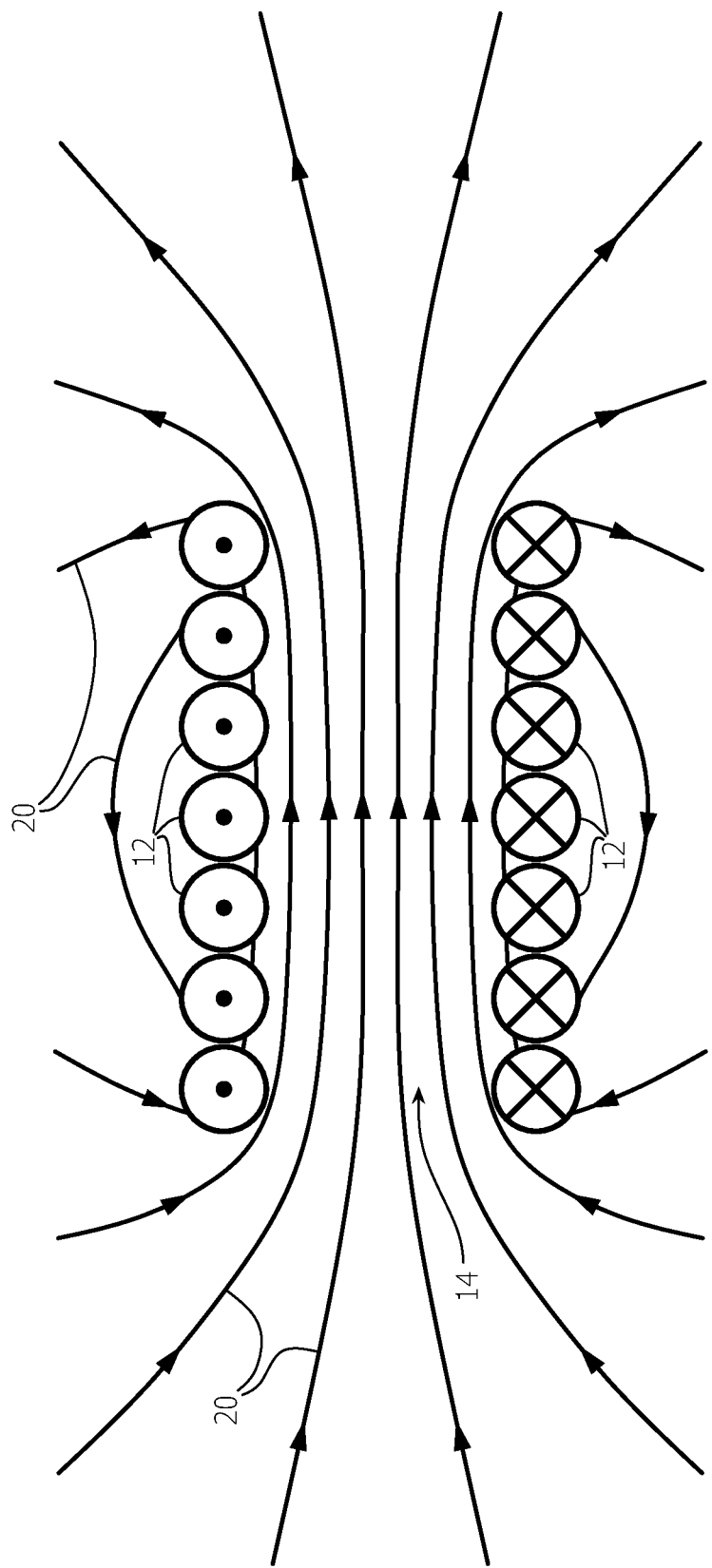
FIG. 2 shows the lines of force of the magnetic field created within the solenoid of FIG. 1 when an electrical current is run through the wire forming a solenoid.

The invention is a device made of a number of interconnected helically wound coils or solenoids which can produce complex three dimensional electrical or magnetic fields for application to various items or bodies or can act as a sensor or antenna to sense complex three dimensional electrical or magnetic fields. A solenoid is a coil of electrically conductive material, such as an electrically conductive wire. and which produces a uniform magnetic field in a volume of space when an electrical current is passed through the electrically conductive material. The length of the solenoid is generally greater than its diameter. FIG. 1 is a schematic representation of a solenoid 10 of the prior art. FIG. 1 shows a copper wire 12 wound into a helical coil which forms the solenoid 10. While a solenoid will generally have windings which are tightly spaced, usually against each other using insulated wire, for illustrative purposes, FIG. 1 shows an embodiment of a solenoid with the windings spaced apart. Such windings may be formed by wrapping the copper wire 12 around a solid and rigid cylindrical core, usually of magnetic material such as iron. However, the solid and rigid cylindrical core material can be removed, if desired to provide the windings as shown forming a straight cylindrical open air core 14 within the solenoid. As shown, the solenoid of FIG. 1 is in a straight cylindrical form. A solenoid will generally have a length which is substantially greater that it's width. When a voltage is connected to the opposite ends 16 and 18 of the wire 12, a current flows through wire 12 and creates a magnetic field within the core 14. FIG. 2 shows the lines of force 20 of the magnetic field which is created when an electrical current is run through the wire 12 forming the solenoid 10 of FIG. 1. A solenoid is a type of electromagnet whose purpose is to generate a controlled magnetic field. Different materials can be used as a core material for the solenoid. The higher the magnetic permeability of the core of the solenoid, the stronger is the magnetic field induced. Ferromagnetic materials with relatively high magnetic permeability are typically used to create strong electromagnetic fields. As shown by FIG. 2, when the solenoid is of straight cylindrical form, the magnetic field formed in the core 14 of the solenoid has substantially straight lines of force. These lines of magnetic force will extend from the end of the solenoid and curve around the outside of the solenoid.

As shown in FIG. 2, a single solenoid provides a magnetic field having substantially straight lines of force within the coil of the solenoid which extend from the ends of the solenoid and curve back around the outside of the coil of the solenoid so join in a closed loop. This does not produce complex magnetic fields or electrical fields within the coil of the solenoid. The idea of this invention is to produce a solenoid device that will provide complex magnetic fields and/or electrical fields within a coil of a solenoid. In general, this is done by combining at least two solenoids into a solenoid structure. The invention provides a primary solenoid, solenoid A, such as shown in FIG. 1, and adds at least a secondary solenoid, solenoid B, to the primary solenoid. The invention creates the secondary solenoid by curving the longitudinal axis of a primary solenoid into a tightly wound helical structure which forms the secondary solenoid. The solenoid structure may or may not be expanded further by continuing to iterate the basic process described above. In the same manner as we coiled the primary solenoid, solenoid A, into a helical structure to form the secondary solenoid, solenoid B, if the secondary solenoid has a high Length/Diameter ratio so is long enough, we may iterate the same process of coiling it around a cylindrically shaped object into yet another helical structure which forms a tertiary solenoid, solenoid C. The space within the secondary solenoid will no longer be cylindrical, but will rather acquire a helical shape, while the space within the tertiary solenoid will be cylindrical.

As we continue the iterative process, and if the L/D ratio of the tertiary solenoid is sufficiently high, we may curve the longitudinal axis of the tertiary solenoid, solenoid C into a fourth order solenoid, solenoid D, and under the same condition, coil that in turn into Solenoids E, F, and G and so on. Each one of these subsequent solenoids will have a structure that contains all of the structures of the previous solenoids, and will be similar to them. At the same time each one would have a space within itself—cores A, B, C, D, E, F, etc., and all would have a helical shape except the last one—the space within the largest solenoid, which is cylindrical. Every solenoid of "higher level" contains the wire and all of the solenoids of "lower level" and their respective cores. For example, the tertiary solenoid C contains the entire wire, the primary and secondary solenoids A and B, and the Cores A, B, and C.

When alternating electricity from an external source X (efX) is applied to the wire of the primary solenoid, solenoid A, an alternating magnetic field (mfA) emerges in its core A. Provided that the core A is preferentially made of magnetic material (material with relatively high magnetic permeability) the ends of which are connected to each other to create a closed loop, this will necessarily induce an alternating electric field (efB) within the core B, which is similar to efX. If core B is made of electro-conductive material and its ends are connected to create a closed loop, this in turn will induce an alternating magnetic field (mfC) in core C similar to mfA, which then will induce efD, mfE, efF, and so on: efX→mfA→efB→mfC→efD→mfE→efF, etc., as long as the cores are made of magnetic and electro-conductive materials in alternating order as described above, and are connected into closed loops. However, the cores of magnetic material do not need to be connected into closed loops.

All induced electric fields may share similarities in frequency and pulse form, and all induced magnetic fields may be similar to each other as well. As mentioned above, the core spaces may be filled with various materials that may or may not increase the induced electric or magnetic fields. It can be seen from above that the alternating cores A, C, E, G, etc. contain induced magnetic fields with lines of force parallel to the axis of the respective core space. Similarly, alternating cores B, D, F, H, etc. contain the electric fields with lines of force parallel to their axes.

Since the core of the largest, highest level solenoid is cylindrical, the lines of force in it, electric or magnetic, will be parallel to its longitudinal axis, and therefore will be represented by straight lines. In a device that has an odd number of levels (1, 3, 5 etc.), the highest level solenoid core will contain a magnetic field with straight lines of force. Similarly, in a device with even number of levels (2, 4, 6, etc.), the highest level core will contain electric field with straight lines of force parallel to the long axis of its cylindrical space.

It would be preferable, although not absolutely necessary, for the odd level cores A, C, E, G, etc. to be made of material with high magnetic permeability, whereas the even level cores B, D, F, H, etc. should be made of material with good electric conductivity. It should be noted here that although the entire device is made of a single copper or other conductive material wire, the cores of solenoids of different levels may be filled with materials that may have different electric properties (conductivity, resistivity, dielectric coefficient, etc.) or magnetic properties (magnetic permeability, coercivity, hysteresis, etc.) that may or may not have some effect on functioning of the solenoid of each level and the entire device as a whole. Further, the electro-magnetic effects within the final core will be created not only by the final coil, but also by the influence from all of the structures of lower levels, potentially creating a complex electro-magnetic environment within that final core.

Figure 3:
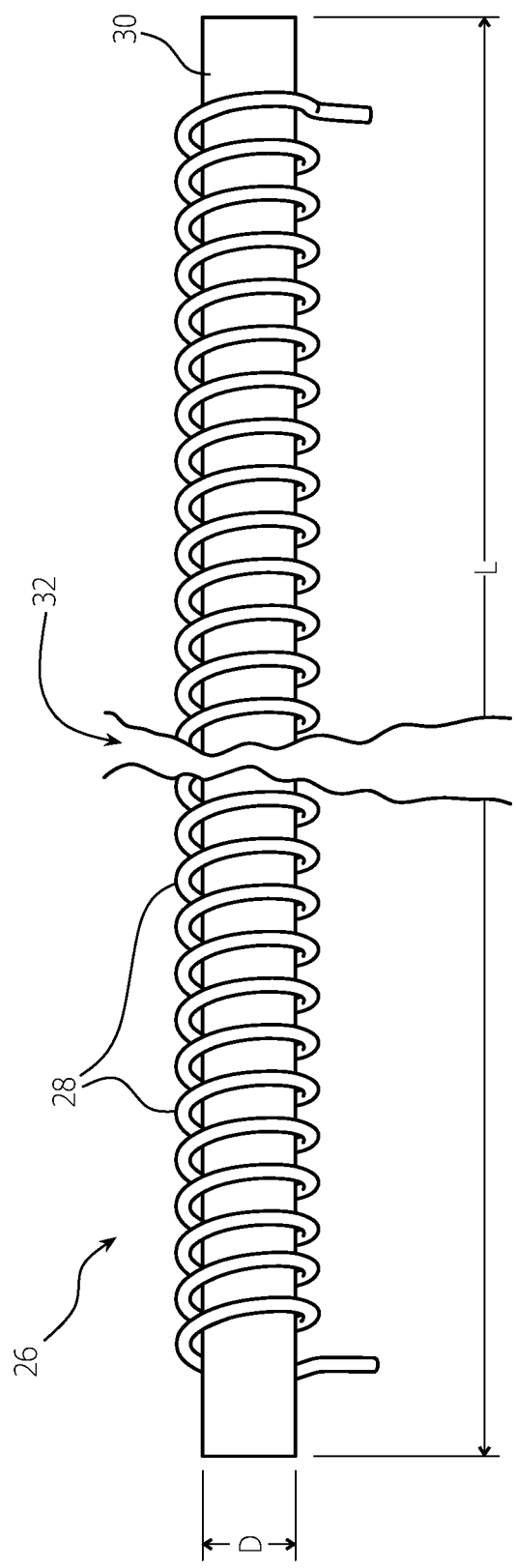
FIG. 3 shows schematically a solenoid similar to that of FIG. 1 but configured for use in constructing a device of the invention.

FIG. 3 shows a solenoid 26 similar to the solenoid 10 of FIG. 1 with the solenoid wire 28 of FIG. 3 wrapped helically around a bendable core such as a length of bendable wire 30 which forms the core for the solenoid 26. For use in forming devices of the invention, the solenoid wire 28 and the core wire 30 of solenoid 26 are flexible or bendable and the length of the solenoid 26 is greater than the diameter of the solenoid 26. This is indicated by the break 32 in the showing of the length of the solenoid 26. It is satisfactory that the length to diameter ratio for solenoid 26 is greater than about one hundred (L/D>>100). This length to diameter ratio is greater than the usual prior art solenoid. Again, this is a schematic showing of the solenoid and windings and for illustration purposes the windings are shown spaced apart but the windings will be tightly spaced, usually against one another using insulated wire 28. Further the relative diameters of the core and the windings are exaggerated. For use in the invention, the solenoid 26 of FIG. 3 will generally form an elongate flexible or at least bendable solenoid structure similar to the wires from which it is formed. Such a solenoid structure can be bent and in such instance, the lines of force created in the core 30 of the solenoid will be bent to follow the shape of the core 30. This solenoid 26 of FIG. 3 can then be helically wound about a second core as shown in FIG. 4 to form a device of the invention.

Figure 4:
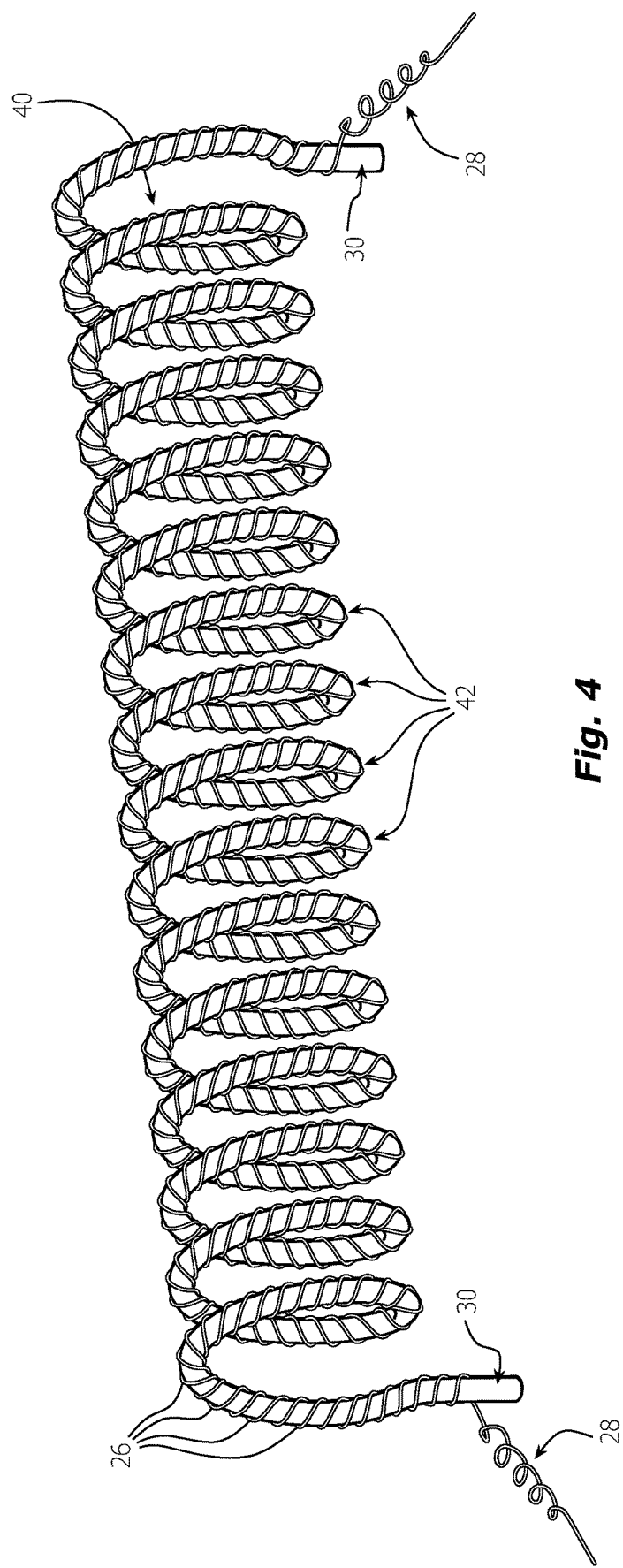
FIG. 4 shows schematically an example of a device of the invention based on a solenoid as shown in FIG. 1, but including two solenoid structures.

FIG. 4 shows schematically an example of a device of the invention. The of FIG. 4 is formed by helically wrapping solenoid 26 of FIG. 3, which can be referred to as the primary solenoid, about an additional core 40, shown in FIG. 4 as an open core. As described for FIG. 3, solenoid 26 is formed by copper wire 28 wrapped helically around a cylindrical core 30 formed by a straight length of wire 30 made of a magnetic material such as an iron wire. The wire 28 wrapped helically around the wire 30 to form the primary helix is also a solenoid around the wire 30, and is referred to as the primary solenoid. The wire 30 which forms the core for the primary helix or solenoid 26 is not rigid so the primary helix or solenoid, indicated as solenoid 26, can be flexed to any desired shape and can be, as shown in FIG. 4, wrapped (coiled) around another cylinder, indicated as core 40 in FIG. 4, to form another helical structure, referred to as a secondary helix or solenoid 42 in FIG. 4. Core 42 in FIG. 4 is shown as an open or air core and could be formed by actually wrapping the primary helix around a cylindrical core which is removed after the secondary helix is wrapped. The structure of the invention shown in FIG. 4, is a helical coil, solenoid 26, coiled into a further helical coil, solenoid 42. If this secondary helix or solenoid 42 as shown in FIG. 4 is long enough and flexible enough, it can be further flexed and wrapped into another helical structure, a tertiary helix. If that tertiary helix is long enough and flexible enough, it can be flexed and wrapped into a further helix and the process can be continued through multiple iterations. In use of the solenoid 42 of FIG. 4, if an electrical current is passed through wire 28, various electrical and magnetic fields are created in secondary open core 40 of solenoid 42 and in the area outside around solenoid 42. A material to be treated by such electrical or magnetic fields can be positioned within open core 40 or can be positioned adjacent to solenoid 42. Similarly, if electrical or magnetic signals from a material are to be detected, the material generating such signals can be placed within open core 40 or adjacent to solenoid 42 and electrical or magnetic signals generated in wires 28 and/or 30 can be detected and measured.

Figure 5:
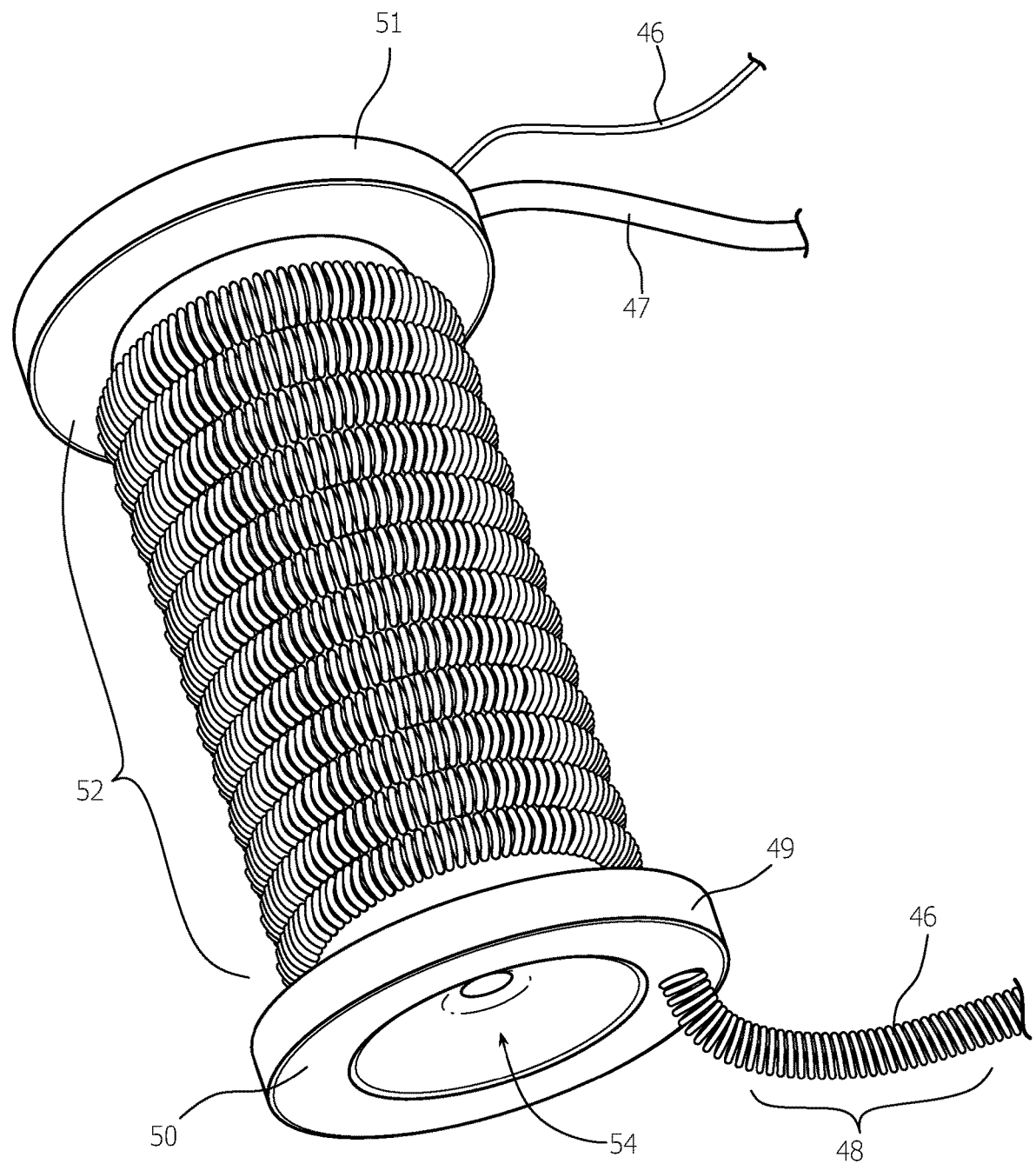
FIG. 5 is a perspective view of a device of the invention.

FIG. 5 shows a prototype example of the device of the invention. A length of copper wire 46 helically and closely wound around a core of iron wire 47 forms a long and flexible solenoid 48 similar to the solenoid 26 of FIG. 3, but having the copper wire windings spaced substantially against one another, forms the primary helix or solenoid 48 of the device of FIG. 5. This long and flexible primary helix or solenoid 48 is then helically wrapped around a cylindrical core spool 50 of plastic material to form a secondary helix or solenoid 52 with the spool forming the core of the secondary helix and having an open center area 54. The primary solenoid 48 is shown extending through a lower end rim 49 of the spool 50 to be wound around spool 50 to form the secondary helix or solenoid 52 with the opposite end of the primary solenoid 48 extending through the upper end rim 51 of the spool. After the primary solenoid extends through upper end rim 51 of spool 50, the copper wire 46 and steel wire 47 separate and copper wire 46 is no longer wound around steel wire 47. These separate wires are shown extending from the upper end rim 51 of the spool. The ends of the copper wire 46 are connected to a source of electricity, not shown, which creates a current flow through the copper wire 46 to create magnetic fields in iron wire 47, i.e., the core of the primary solenoid 48, which then causes an electrical field and magnetic field to be created in the coil space 54 which forms the core of the secondary solenoid 52. Thus, when an electrical current is passed through wire 46 forming primary solenoid 48, various electrical and magnetic fields are created in the center open area 54 of secondary core spool 50, and in the area around the outside of secondary helix 52. Spool opening 54 forms a chamber into which a material to be treated by such electrical or magnetic fields can be positioned within the core area of secondary helix 52 or can be positioned adjacent to secondary helix 52. Similarly, if electrical or magnetic signals from a material are to be detected, the material generating such signals can be placed within spool opening 54 or adjacent to secondary helix 52 and electrical or magnetic signals generated in wire 46 can be detected and measured.

Figure 9:
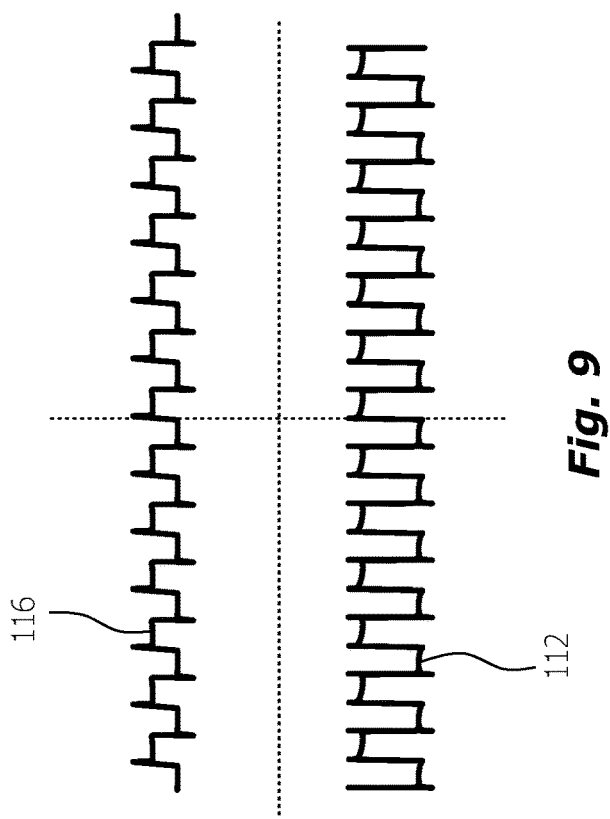
FIG. 9 shows oscilloscope screen tracings of input signals to a device of the invention and resultant output signals for an additional test of the invention.
Figure 8:
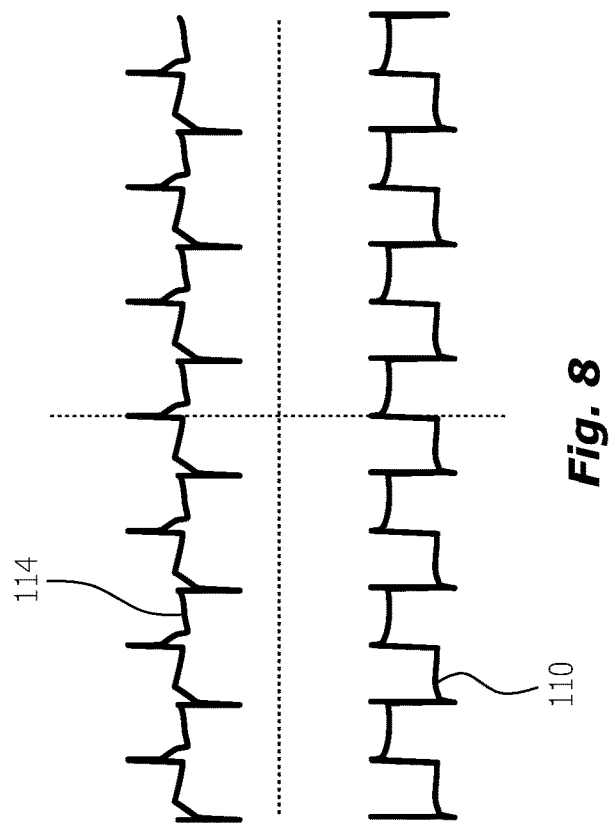
FIG. 8 shows oscilloscope screen tracings of input signals to a device of the invention and resultant output signals for a test of the invention.

In a use of the device of FIG. 5, a long cylindrical glass tube with rubber stoppers on both ends was filled with a solution to mimic the intracellular environment. Conductive metal wire electrodes were inserted on both sides of the glass tube through the rubber stoppers so that their ends come in contact with the solution within the tube. The tube was then inserted into the coil space 54 within the secondary solenoid 52 and the metal electrodes were connected to an oscilloscope. The ends of the copper wire 46 forming the primary solenoid were connected to a signal generator. Quasi rectangular AC electrical signals of given frequency were applied to the ends of copper wire 46. Similarly shaped (quasi-rectangular) electric current of the same frequency was registered at the same time on the Oscilloscope. The lower signal traces 110 in FIGS. 8 and 112 in FIG. 9 show signals as applied to the copper wire. The upper signal traces 114 in FIGS. 8 and 116 in FIG. 9 show signal traces of the resultant signals from the solutions in the tubes in the coil space 54 of the core 54 of secondary solenoid 52. This confirms the emergence of alternating electric current within the solution in core 54 of secondary solenoid 52 without a direct contact (electrode, wire) with such solution, and in response to application of similar electric current to the wire 46 of the primary solenoid 48.

Figure 6:
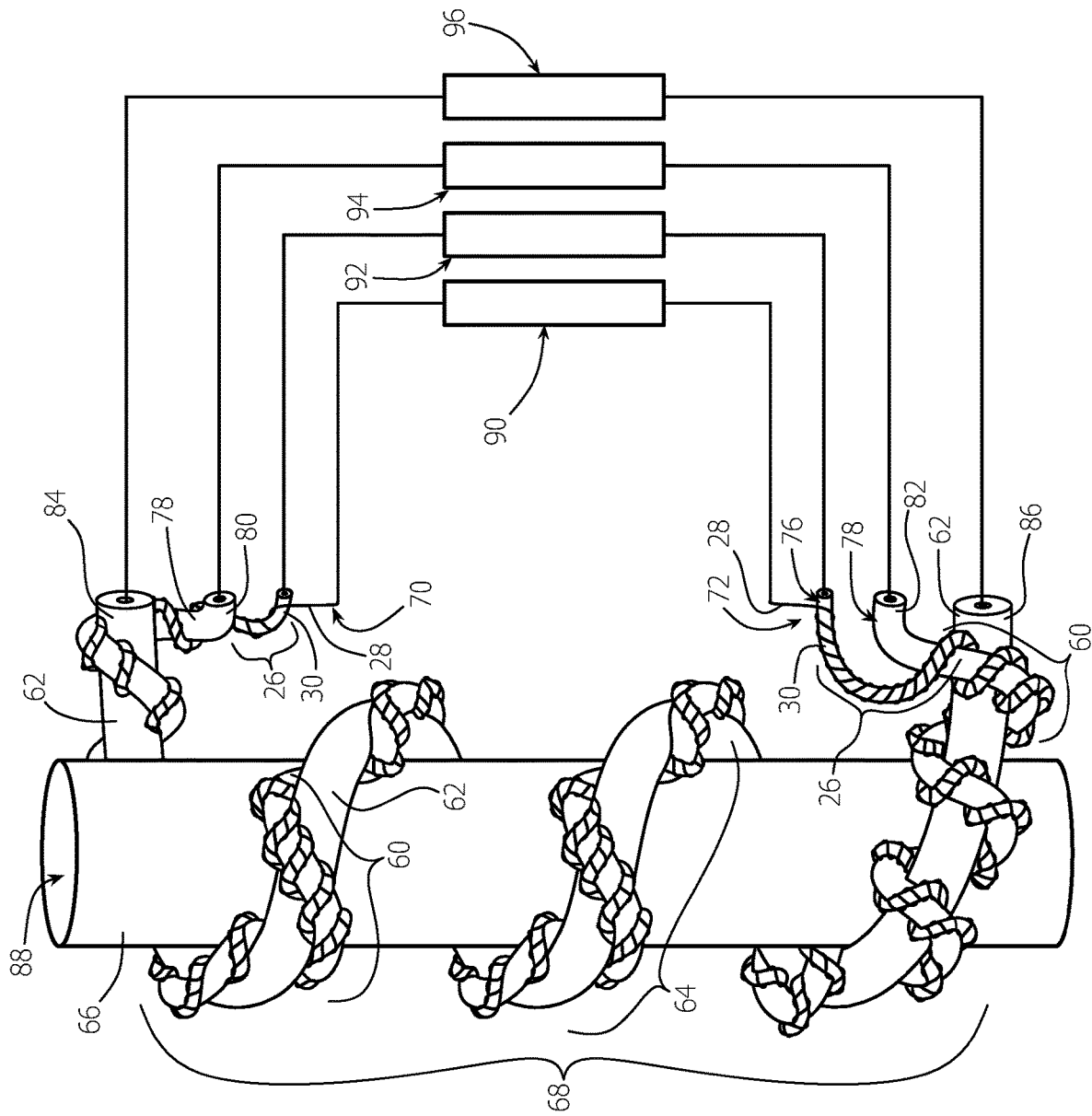
FIG. 6 shows schematically a further embodiment of a device of the invention and shows example wiring connections for the device.

FIG. 6 shows schematically an example of a device of the invention using a secondary solenoid 60 similar to the secondary solenoid 42 of FIG. 4, helically wound around an additional tertiary core 62 to form a tertiary solenoid 64, which is then helically wound around an additional core 66 to form a fourth order solenoid 68. FIG. 6 also shows possible connections of the wires forming the various solenoids and cores. As shown in FIGS. 4 and 6, the wire 28 with ends 70 and 72, FIG. 6, is helically wrapped around wire core 30 with ends 74 and 76, FIG. 6, to form the primary helix or solenoid 26. Primary solenoid 26 is then helically wrapped around core 78 to form secondary solenoid 60. Secondary solenoid 60 with wire core 78 having wire ends 80 and 82 is helically wrapped around tertiary wire core 62 with ends 84 and 86 to form a third or tertiary solenoid 64. This third solenoid 64, is then helically wrapped around a hollow cylinder 66, such as a plastic tube, which forms a core for a fourth solenoid 68. Thus, FIG. 6 shows a device of the invention having four levels of helixes. Hollow cylinder 66, having a hollow opening 88 extending therethrough, provides a receiving chamber to receive material to be treated by the electrical and/or magnetic fields generated by the combination of solenoids surrounding it.

Materials and connections for the various wires and cores for the four level embodiment of FIG. 6 can be as follows:

Wire 28 with ends 70 and 72—Main wire 28 forming the primary solenoid 26 is copper or other electro-conductive material. The ends 70 and 72 of wire 28 are connected to a source of electricity 90 to provide an electric current in wire 28 so that primary solenoid 26 will generate magnetic fields in primary core 30.

Core 30 with ends 74 and 76—Core 30 forming the primary core for primary solenoid 26 is iron or other magnetic material. The ends 74 and 76 of core 30 are connected together at connection 92 to form a magnetic short circuit between the ends 74 and 76 for the flow of magnetic fields in core 30. Connection 92 can also be or include a device that can serve as source of magnetism, as an amplifier to amplify the magnetic forces flowing in core 78, or to otherwise modify the magnetic fields flowing in core 78. Further, the ends 74 and 76 of core 30 can be left unconnected as the magnetic field generated in core 30 will extend through the air between the respective ends 74 and 76.

Core 78 with ends 80 and 82—Core 78 forming the secondary core for secondary solenoid 60 is copper or other electro-conductive material. The ends 80 and 82 of core 78 are connected together at connection 94 to form an electrical short circuit between the ends of core 78 for the flow of electrical current in core 78. Connection 94 can also include a device that can serve as a source of electricity, as an amplifier to amplify the electrical current flowing in core 78, or to otherwise modify the electrical signals flowing in core 78.

Core 62 with ends 84 and 86—Core 62 forming the tertiary core for tertiary solenoid 64 is iron or other magnetic material. The ends 84 and 86 of core 62 are connected together at connection 96 to form a magnetic short circuit between the ends for the flow of magnetic fields in core 62. Connection 96 can also be or include a device that can serve as source of magnetism, as an amplifier to amplify the magnetic forces flowing in core 62, or to otherwise modify the magnetic fields flowing in core 62. Again, since core 62 will primarily have magnetic signals flowing therein, the ends 84 and 86 of core 62 can be left unconnected as the magnetic field generated in core 62 will extend through the air between the respective ends 84 and 86.

Core 66 forming the fourth order core for the fourth order solenoid 68 provides a hollow core 88 so can be merely a hollow or air core, or as shown, can be a hollow tube 66 of plastic or other non-electric or non-magnetic material having a hollow central opening 88 so that the electrical or magnetic fields created by fourth order solenoid 68 pass through the material forming tube 66 and are created in the open area of core 66. Material to be treated by the electric fields or magnetic fields created by the device of the invention are placed in the open area 88 or near the outside of the device so that the electric fields or magnetic fields will create the desired electric current in the material to be treated or other desired effects of the electric fields and magnetic fields will be created in the material to be treated.

Figure 7:
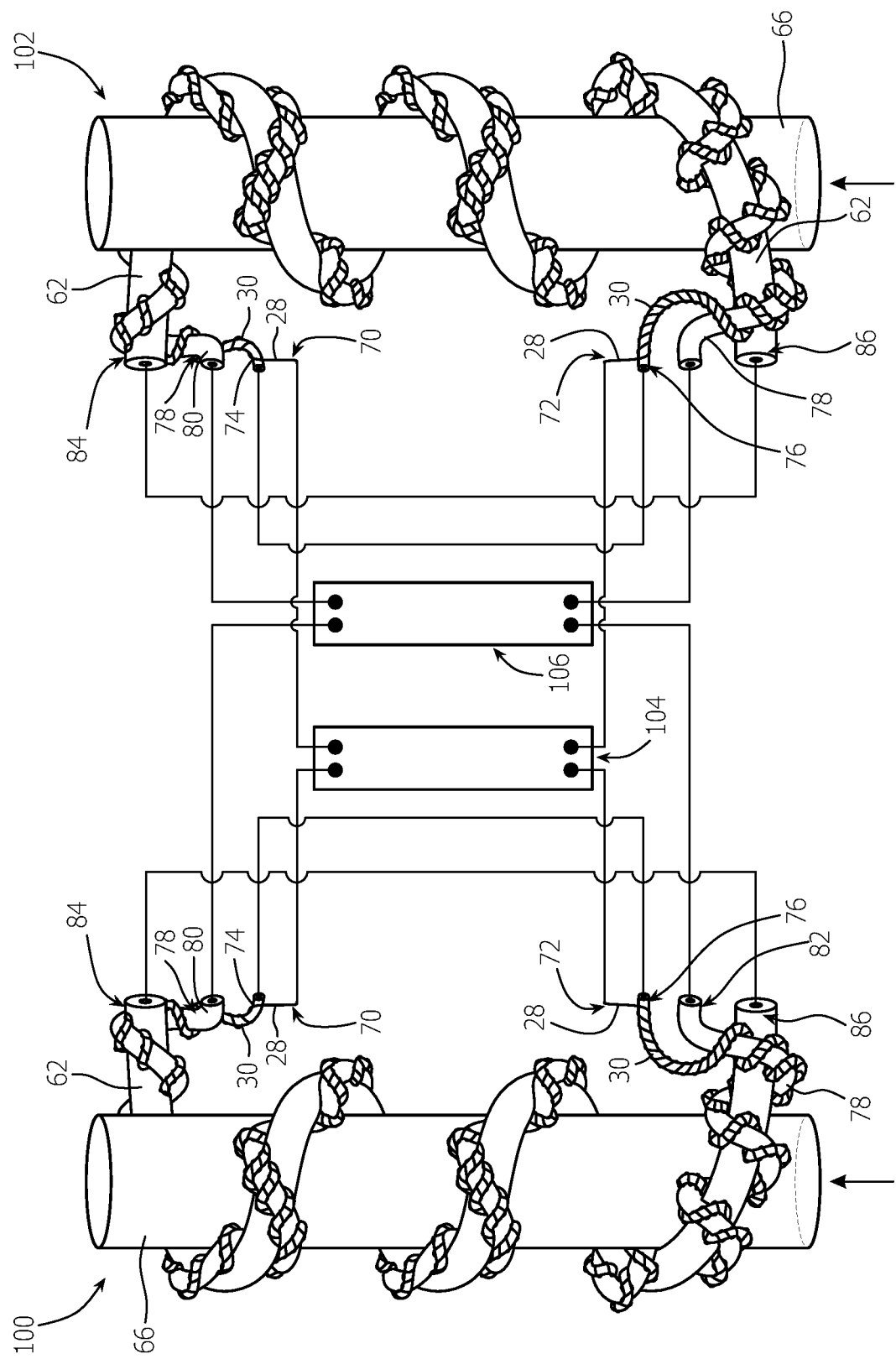
FIG. 7 shows schematically an arrangement of two separate identical devices of the invention and how the two devices can be interconnected to transfer information regarding an item in one of the devices to an item in the other device.

FIG. 7 shows two separate devices as shown in FIG. 6 connected together. The first device 100 is connected to second device 102 either directly (corresponding wire-to-corresponding wire) or via some electronic device (104, 106) such as an amplifier, a filter, or some other device that could serve as a source of current or electro-magnetism or could alter it. In the embodiment of FIG. 7, the ends 74 and 76 of core 30 of each device 100 and 102 are directly connected together, and the ends 84 and 86 of core 62 of each device 100 and 102 are connected directly together making them separate closed loops in each device made of iron or other magnetic material. Alternately, such cores could be left open and not connected. On the other hand, the ends 70 and 72 of the main wire 28, and the ends 80 and 82 of core 78 of device 100 are connected to the same ends 70 and 72 and 80 and 82 of the main wire 28 and core 78 of device 102 via electronic devices 104 and 106. The electromagnetic fields of one device will therefore be transferred to the other device. Such an arrangement of two separate similar devices 100 and 102 may be useful, for example, when it is desired to transfer or copy electromagnetic fields from one item to a second similar second item, such as from one body organ, part, or cell to a second replacement body organ, part, or cell. Device 100 may serve as a receiver/antenna in the pair of devices where the item from which the electromagnetic fields to be copied is placed, and device 102 may serve as a transmitter to transmit the copied electromagnetic fields to the second or replacement item.

To create electrical fields or magnetic fields, the material used to create each of the helical coils will be an electrically conductive material such as a wire, for example, a copper wire. While the wire used to build the entire construct is made of the same material at every level of organization, the cylindrical core around which each helix is wound can be made of different materials with different physical properties, and can have different diameters and lengths.

The geometry of the structure of the devices of the invention is interesting in several different ways, one of which is self-similarity. This geometry is known as Fractal Geometry, which describes objects with dimension that are represented by a fractional rather than a whole (natural) number as in classical Euclidian Geometry. For example, an object can have a dimension=2.67, it would be neither 2-dimensional, nor 3-dimensional. One of the important qualities of fractals is the ability to "fit" a large surface area into a relatively small volume. Similarly, a large length can be fit into a small volume. These are some of the important qualities of this structure, and they may offer numerous possible applications. The devices of this invention can be described as electro-magnetic coil device that have a geometry such that when electricity is applied to the ends of the wire it's made of, in certain embodiments of the coil, it allows the creation of spatially (3-dimensionally) complex EM fields with lines of force of desired shape and direction within a defined space. The resultant electric fields have lines of force that can be either straight or, if desired, curved in predetermined manners, which would be defined by the geometry of the coil itself. If the electricity applied to the wire is AC, the induced magnetic field within that space will also have lines of force that are either straight or curved in predetermined manner. The space within the coil in which these lines of force of induced electric or magnetic fields emerge, may contain cells, tissues, organs, parts of the body, or the entire body, or any other items or objects of interest, which will in that case be exposed to, and effected by these electric and magnetic fields without coming into a direct mechanical contact with the coil and with the wire it is made of, which can assure the emergence of electric or magnetic fields in desired predetermined direction within these cells and tissues. This may be particularly important for cells, tissues and organs that have a clear axial orientation (myocytes, retinal cells, eyes, blood vessels, long bones, nerves, skin, etc.). Some cells, tissues and organs even have an intrinsic electrical polarity to them, so the direction in which the electric signal is flowing may be important for achieving a desired effect.

Whereas the invention is here illustrated and described with reference to embodiments thereof presently contemplated as the best mode of carrying out the invention in actual practice, it is to be understood that various changes may be made in adapting the invention to different embodiments without departing from the broader inventive concepts disclosed herein and comprehended by the claims that follow:

The invention claimed is:

1. An elongate structure for generating or detecting electrical and/or magnetic signals or fields, said structure having separate spaced apart ends, comprising;
    a primary helical winding including a primary thread wrapped helically around a primary core; said primary thread being electrically conductive and said primary core having a high magnetically permeability, and
    an additional helical winding forming a secondary helical winding wherein the secondary helical winding is formed by the primary helical winding wrapped helically around a secondary core, wherein the secondary core is electrically conductive and the ends of the secondary core are electrically connected.

2. The elongate structure of claim 1, wherein the electrically conductive primary thread is an electrically conductive wire.

3. The elongate structure of claim 2, wherein the primary core is formed of a material having a high magnetic permeability.

4. The elongate structure of claim 3, wherein the material with high magnetic permeability is iron wire.

5. The elongate structure of claim 3, wherein the ends of the primary core are connected with a material having high magnetic permeability.

6. The elongate structure of claim 1, wherein electrical and/or magnetic fields are generated in the secondary core and wherein the secondary core includes a receiving chamber to receive material to be treated by the electrical and/or magnetic fields generated in the receiving chamber included in the secondary core.

7. The elongate structure of claim 1, wherein the secondary core includes a receiving chamber to receive an item generating electrical and/or magnetic fields to be detected, and wherein the electrical and/or magnetic fields generated by the item received in the receiving chamber are detected by the secondary and primary cores and secondary and primary windings surrounding the receiving chamber.

8. The elongate structure of claim 1, additionally comprising:
    an additional helical winding forming a tertiary helical winding having spaced apart ends, wherein the tertiary helical winding is formed by the secondary helical winding wrapped helically around a tertiary core, wherein the tertiary core has a high magnetic permeability.

9. The elongate structure of claim 8, wherein the ends of the tertiary core are connected with a material having high magnetic permeability.

10. The elongate structure of claim 8, wherein electrical and/or magnetic fields are generated in the tertiary core and wherein the tertiary core includes a receiving chamber to receive material to be treated by the electrical and/or magnetic fields generated in the receiving chamber included in the tertiary core.

11. The elongate structure of claim 8, wherein the tertiary core includes a receiving chamber to receive an item generating electrical and/or magnetic fields to be detected, and wherein the electrical and/or magnetic fields generated by the item received in the receiving chamber are detected by the tertiary, secondary, and primary cores and tertiary, secondary, and primary windings surrounding the receiving chamber included in the tertiary core.

12. The elongate structure of claim 8, additionally comprising:
an additional helical winding forming a fourth order helical winding having spaced apart ends, wherein the fourth order helical winding is formed by the tertiary helical winding wrapped helically around a fourth order core, wherein the fourth order core is electrically conductive and the ends of the fourth order core are electrically connected.

13. The elongate structure of claim 12, wherein electrical and/or magnetic fields are generated in the fourth order core and wherein the fourth order core includes a receiving chamber to receive material to be treated by the electrical and/or magnetic fields generated in the receiving chamber included in the fourth order core.

14. The elongate structure of claim 12, wherein the fourth order core includes a receiving chamber to receive an item generating electrical and/or magnetic fields to be detected, and wherein the electrical and/or magnetic fields generated by the item received in the receiving chamber are detected by the fourth order, tertiary, secondary, and primary cores and fourth order, tertiary, secondary, and primary windings surrounding the receiving chamber.

15. The elongate structure of claim 12, additionally comprising;
at least one additional helical winding forming an additional order helical winding having spaced apart ends, wherein the additional order helical winding is formed by the immediately prior stage helical winding wrapped helically around an additional order core, wherein the additional order core has either a high magnetic permeability or is electrically conductive so as to be different from the immediately preceding order core, and if electrically conductive, the ends of the electrically conductive core are electrically connected.

16. The elongate structure of claim 15, wherein if the additional order core has a high magnetic permeability, the ends of the additional order core are connected with a material having high magnetic permeability.

17. The elongate structure of claim 12, wherein electrical and/or magnetic fields are generated in the additional order core and wherein the additional order core includes a receiving chamber to receive material to be treated by the electrical and/or magnetic fields generated in the receiving chamber included in the additional order core.

18. The elongate structure of claim 15, wherein the additional order core includes a receiving chamber to receive an item generating electrical and/or magnetic fields to be detected, and wherein the electrical and/or magnetic fields generated by the item received in the receiving chamber are detected by the additional orders, fourth order, tertiary, secondary, and primary cores and additional orders, fourth order, tertiary, secondary, and primary windings surrounding the receiving chamber.

19. A device for transferring complex electrical and/or magnetic signals or fields from one item to a second item, comprising two of the elongate structures of claim 8 each with a receiving chamber in the tertiary core for either receiving an item to be treated by the electrical and/or magnetic fields generated in the receiving chamber or for detecting electrical and/or magnetic fields produced by an item in the receiving chamber, the respective secondary cores of the two elongate structures connected together and the respective primary threads of the two elongate structures connected together by electrically conductive connections, whereby the electric and magnetic fields detected for the item in one of the receiving chambers are transferred to the item received in the other receiving chamber.

20. A device for transferring complex electrical and/or magnetic signals or fields from one item to a second item, comprising two of the elongate structures of claim 1 each with a receiving chamber in the secondary core for either receiving an item to be treated by the electrical and/or magnetic fields generated in the receiving chamber or for detecting electrical and/or magnetic fields produced by an item in the receiving chamber, the respective secondary cores of the two elongate structures connected together and the respective primary threads of the two elongate structures connected together by electrically conductive wires, whereby the electric and magnetic fields detected for the item in one of the receiving chambers are transferred to the item received in the other receiving chamber.

* * * * *